United States Patent [19]

Hanson et al.

[11] Patent Number: 4,766,242

[45] Date of Patent: Aug. 23, 1988

[54] SYNTHESIS OF SUBSTITUTED ARYL SULFIDES

[75] Inventors: Harry T. Hanson, Millburn, N.J.; John B. Sapp, Jr., Houston, Tex.

[73] Assignee: Hoechst Celanese Corporation, Somerville, N.J.

[21] Appl. No.: 344,335

[22] Filed: Feb. 1, 1982

[51] Int. Cl.$^4$ .................................. C07C 103/19
[52] U.S. Cl. .................................. 564/154; 564/156; 564/162
[58] Field of Search .................. 564/430, 162, 156; 252/429 B; 568/23

[56] References Cited

U.S. PATENT DOCUMENTS

| | | | |
|---|---|---|---|
| 2,345,239 | 3/1944 | Cook et al. | 564/430 X |
| 2,434,396 | 1/1948 | Cook et al. | 564/430 |
| 3,100,765 | 8/1963 | Albert | 564/430 X |
| 3,156,728 | 11/1964 | Orloff et al. | 564/430 |
| 3,479,407 | 11/1969 | Laufer | 568/23 |
| 3,624,000 | 11/1971 | Throckmorton | 252/429 B |
| 3,844,956 | 10/1974 | Nnadi | 564/430 X |
| 3,912,707 | 10/1975 | Abbott et al. | 568/23 X |

OTHER PUBLICATIONS

Dale et al., "J. Chem. Soc. Chem. Comm.", pp. 295–296 (1976).

Primary Examiner—Robert V. Hines
Attorney, Agent, or Firm—Burns, Doane, Swecker & Mathis

[57] ABSTRACT

Provided is a novel and effective process for the synthesis of aryl sulfides substituted with an alkanoylamino or (N-alkyl)alkanoylamino substituent. The process comprises reacting an appropriately substituted aromatic compound with a sulfur dihalide, preferably sulfur dichloride, in the presence of an alkali metal tetrafluoroborate catalyst and an ether comprising solvent.

19 Claims, No Drawings

SYNTHESIS OF SUBSTITUTED ARYL SULFIDES

BACKGROUND OF THE INVENTION

1. Field Of The Invention

This invention relates to a process for the production of substituted aryl sulfides. More particularly, this invention relates to a process for the production of alkanoylamino or (N-alkyl)alkanoylamino substituted aryl sulfides, such as bis(p-acetylated amine) substituted diaryl sulfides, by employing an alkali metal tetrafluoroborate catalyst.

2. Background Of The Invention

A wide variety of aryl sulfides, and in particular diaryl sulfides, are known, the utilities of which are just as varied. For example, aryl and in particular diaryl sulfides are known to be useful as intermediates, especially for the preparation of insecticides, as plasticizers, high boiling solvents, heat exchange fluids, and hydraulic fluids.

A well-known class of substituted diaryl sulfides is that of the hydroxy substituted diaryl sulfides, or thiobisphenols, same generally finding utility as intermediates or as oxidation inhibitors. One generally known process for preparing hydroxy substituted diaryl sulfides, or thiobisphenols, is by reacting a phenol with a sulfur chloride compound.

For example, U.S. Pat. No. 4,056,568 discloses the reaction of a 3,5-dialkyl phenol with a sulfur chloride compound to form a sulfenyl chloride. Subsequent reaction thereof with a phenol produces a diaryl monosulfide.

U.S. Pat. No. 3,718,699 discloses a process of preparing 4,4'-dithiobis(2,6-di-t-butylphenol). Said process comprises reacting 2,6-di-t-butylphenol with sulfur monochloride in the absence or presence of a catalytic amount of iron powder or a Lewis acid.

U.S. Pat. No. 3,129,213 discloses a process wherein an orthoalkylphenol is reacted with sulfur dichloride to form a reaction product suitable for use as an antioxidant and/or antiwear agent. U.S. Pat. No. 3,057,926 discloses a process wherein an alkyl or alkoxy substituted phenol is reacted with sulfur dichloride. Alternatively, the process may comprise the reaction of an alkali metal salt of the substituted phenol with sulfur dichloride. Neither reaction, however, is conducted in the presence of a conventional catalyst.

Similarly, U.S. Pat. Nos. 2,139,321; 2,370,756; and 2,971,968 disclose the preparation of thiobisphenols by reacting an alkyl phenol with a sulfur chloride compound in the absence of a catalyst.

U.S. Pat. No. 2,402,685, however, discloses reacting a phenol with sulfur dichloride in the presence of a "sulfurization catalyst" to produce a diaryl monosulfide product. Examples of suitable "sulfurization catalysts" include aluminum chloride, bismuth chloride, iron chloride, mercuric chloride, tin chloride, antimony chloride, tantallum pentachloride, titanium tetrachloride and zinc chloride.

While numerous processes are thus known for preparing hydroxy substituted aryl sulfides, the prior art is devoid of a truly suitable process for the formation of aryl sulfide compounds, and in particular diaryl sulfides, wherein the aromatic rings are substituted, particularly in the para positions, with a more complex electron releasing group, such as an alkanoylamino substituent, e.g., an acetylated amine. Such a process, especially if given to high reaction rates and yields, would find ready acceptance by the industry for the preparation of such compounds, which find utility as aromatic monomers, precursors, epoxy curing agents, cure accelerators, etc.

Accordingly, it is an object of the present invention to provide a novel process for preparing substituted aryl sulfides, and in particular, alkanoylamino and (N-alkyl)alkanoylamino substituted aryl sulfides, in good yields and at a high reaction rate.

It is another object of the instant invention to provide a novel process for the production of substituted diaryl sulfides, and in particular, diaryl sulfides substituted in the para positions with an acetylated amine.

Another object of the instant invention is to provide an effective process for synthesizing a bis(p-acetylated amine) diaryl sulfide via a coupling reaction.

Still another object of the instant invention is to provide a process for producing sulfides in high yields, with high reaction rates, and with high selectivity.

These and other objects, as well as the scope, nature and utilization of the invention, will be apparent to those skilled in the art from the following description and the appended claims.

SUMMARY OF THE INVENTION

It has now been unexpectedly and most surprisingly discovered that aryl sulfides substituted with alkanoylamino or (N-alkyl)alkanoylamino substituents can be produced at a high reaction rate and in good yields by reacting a sulfur dihalide, preferably sulfur dichloride, with an aromatic compound of the structural formula

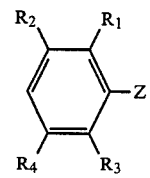

wherein $R_1$, $R_2$, $R_3$, $R_4$, which can be the same or different, represent hydrogen or a lower alkyl, and Z is

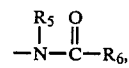

$R_5$ representing hydrogen or a lower alkyl and $R_6$ a lower alkyl, i.e., from 1–6 carbon atoms, in the presence of a catalytic amount of an alkali metal tetrafluoroborate catalyst and an ether comprising solvent capable of solvating said reactants and catalyst sufficiently to allow said reacting to occur.

Diaryl or oligomeric products may efficiently be produced by the instant invention. An oligomeric product, i.e., containing up to about 50 aryl units, is produced by employing a molar ratio of aromatic reactant to sulfur dihalide of greater than 1:1 but less than about 2:1, whereas the substituted diaryl sulfides are obtained by employing a molar ratio of aromatic reactant compound to sulfur dihalide of at least about 2:1.

In a preferred embodiment of the instant invention, 4,4'-diacetamidodiphenyl sulfide is prepared via the process of the instant invention by employing acetanilide as the aromatic compound reactant.

DETAILED DESCRIPTION OF THE INVENTION

The process of the instant invention provides one with a relatively fast, effective, and simple process for preparing aryl sulfides substituted with alkanoylamino or (N-alkyl)alkanoylamino substituents, and in particular, diaryl sulfides substituted in the para positions.

In preparing diaryl sulfides, the process of the instant invention is essentially a coupling reaction which can be depicted schematically as follows:

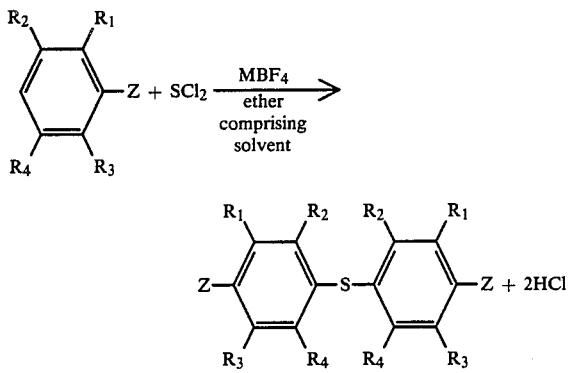

wherein $R_1$, $R_2$, $R_3$ and $R_4$, being either the same or different, represent a substituent which does not interfere with or adversely affect the reaction, for example, hydrogen or a lower alkyl, i.e., an alkyl containing from 1 to 6 carbons, and Z being an alkanoylamino or (N-alkyl) alkanoylamino substituent of the structural formula

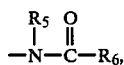

wherein $R_5$ represents a hydrogen or a lower alkyl and $R_6$ a lower alkyl. It is preferable that $R_1$, $R_2$, $R_3$, $R_4$, and $R_5$, being the same or different, are selected from the group consisting of hydrogen and methyl, and most preferably, are all hydrogen with $R_6$ being a methyl.

Respecting the position para from the alkanoylamino or (N-alkyl)alkanoylamino substituent in the aromatic reactant compound of the instant process, it is preferred that said position always remain unsubstituted with anything but hydrogen. This allows for one to take advantage of the paracoupling specificity of the instant process, as it has been found that the process of the instant invention exhibits near quantitative selectivity to the bis(p-substituted) diaryl sulfide product, as depicted in the schematic.

Oligomers containing more than 2 aryl units and up to about 50 aryl units are produced, of course, when the coupling reaction is continued to produce a longer chain. The molar ratio of the aromatic reactant to sulfur dihalide reactant determines the product obtained, with diaryl products being produced quickly and effectively when the molar ratio is at least about 2:1 and oligomers being generally produced when the molar ratio is greater than 1:1 but less than 2:1.

Suitable aromatic compound reactants for the purposes of the process of the instant invention are exemplified by, but not limited to, acetanilide; N-methylacetanilide; 2-methylacetanilide; 3-ethylacetanilide; N-ethylacetanilide; 2,5-dimethylacetanilide; 3,5-dimethyl-N-methylacetanilide; propionanilide and N-methylpropionanilide.

A most preferred aromatic compound reactant for the process of the subject invention is acetanilide, as the instant process has been found most suitable for coupling acetanilide with a sulfur dihalide to form the valuable diaryl sulfide 4,4'-diacetamidodiphenyl sulfide, which is useful as a precursor in providing the valuable chemical compound of thiodianiline, i.e., 4,4'-diaminodiphenyl sulfide.

It is preferred that the sulfur dihalide reactant be of high purity, e.g., containing less than 5 percent by weight of impurities. Such sulfur dihalides are commercially available. The most preferred sulfur dihalide for use in the process of the present invention is sulfur dichloride, which is an easily isolated, stable compound.

The reaction of the present invention is necessarily conducted in the presence of a catalytic amount of an alkali metal tetrafluoroborate catalyst, as represented by $MBF_4$, with M representing an alkali metal selected from the group consisting of lithium and sodium. It has been found that only lithium and sodium tetrafluoroborate are catalytically effective for coupling an alkanoylamino or (N-alkyl)alkanoylamino substituted aromatic compound in accordance with the instant invention to thereby produce the corresponding aryl sulfide, whether a diaryl sulfide or oligomer. Sodium tetrafluoroborate has been found to be the most effective catalyst in terms of yield and reaction rate, and is thus the most preferred catalyst. The lithium and sodium salts of tetrafluoroboric acid are well known, and are commercially available.

The amount of catalyst employed is generally any amount sufficient to effectively bring about a catalytic effect in the reaction, i.e., a catalytic amount. Although any effective amount of catalyst may be employed, it is generally preferred that such effective amount constitute from about 10 to about 300 mole percent based on the molar amount of sulfur dihalide employed, and most preferably from about 150 to about 250 mole percent of catalyst based on the molar amount of sulfur dihalide. Lower levels of catalyst can be employed and are effective, but the reaction rate generally decreases at such low levels as the catalyst level decreases.

The solvent employed is an ether comprising solvent capable of solvating the catalyst and the reactants, i.e., the aromatic compound and the sulfur dihalide, sufficiently to provide a medium for reaction and allow for the reaction to effectively occur under the particular reaction conditions employed without interfering with said reaction. Thus, the solvent is necessarily inert regarding the reaction. The amount of solvent employed is generally an amount sufficient to solvate the reactants and catalyst, with the upper limit of said amount being controlled by the practical limitations of chemical kinetics, i.e., insuring that the concentrations of reactants and catalyst in the reaction medium are not so small as to adversely affect the rate of reaction and/or yield.

By ether comprising solvent is meant that the solvent can comprise a suitably inert ether alone, or an ether in combination with any other suitably inert solvent, which is preferably a halogenated hydrocarbon. Examples of suitable ether solvents include glyme [ethylene glycol dimethyl ether], diglyme [diethylene glycol dimethyl ether], triglyme [triethylene glycol dimethyl ethere] and mixtures thereof. Suitable halogenated hydrocarbons which can be employed in mixtures with a suitable ether are exemplified by 1,2-dichloroethane, chloroethane, dibromoethane, propylene dichloride and chloroform. Examples of suitable ether comprising solvent mixtures include mixtures of 1,2-dichloroethane and triglyme; 1,2-dichloroethane and diglyme; and chloroethane and triglyme.

When a halogenated hydrocarbon-ether mixture is employed as the solvent, the volume percent of said mixture of halogenated hydrocarbon can be about 90% or less. Preferably, however, the mixture comprises a volume ratio of halogenated hydrocarbon to ether in the range of about 1:1 to 5:1, more preferably in the range of about 2:1 to 4:1, and most preferably about 3:1, as solvent mixtures in the above ranges have been found to provide good results with regard to reaction rate and yield.

In conducting the reaction, the molar ratio of the aromatic reactant compound to the sulfur dihalide reactant will vary depending upon the type of product desired. Oligomers are obtained when a molar ratio of greater than 1:1 and less than 2:1 is employed, with the chain being generally shorter the closer the molar ratio is to 2:1. Dimeric products, i.e., diaryl sulfides, are prepared when a molar ratio of at least about 2:1 is employed. An excess of aromatic compound reactant, so that the molar ratio exceeds 2:1, can be used and is not harmful to the instant invention, but generally is not preferred due to possible complications in product isolation.

The reaction can be conducted in any suitable reaction vessel which can be maintained free of water or water vapor. This is to avoid the deleterious reaction of the sulfur dihalide with water, as sulfur dichloride, for example, is very reactive to water in any form. The reaction vessel is also preferably equipped with a conventional stirrer as the reaction is preferably run under agitation.

Hydrogen chloride gas is evolved as a by-product of the reaction, thus, in commercial operations, where recovery of said hydrogen chloride by-product gas is desired, the reaction can be conducted in a vessel equipped with suitable recovery means. Furthermore, an inert gas sweep, e.g., employing gases such as nitrogen, argon, etc., can be used to aid in removing the hydrogen chloride gas evolved.

The addition of the aromatic compound and sulfur dihalide reactants, the ether comprising solvent and alkali metal tetrafluoroborate catalyst to the reaction vessel need be in no particular order. It is preferred, however, that the aromatic reactant compound and tetrafluoroborate catalyst be dissolved and/or suspended in the ether comprising solvent, with the sulfur dihalide then being added slowly, preferably dropwise.

The reaction temperature, if so desired, may be monitored by any conventional means, e.g., a thermocouple. The reaction temperature employed can be any effective temperature, but is preferably below about 110° C. due to the low boiling point of sulfur dihalides, e.g., sulfur dichloride (ca. 60° C.). Thus it is preferred that the reaction temperature employed is in the range of about 0° to 110° C., more preferably in the range of about 25° C. [about ambient temperature] to about 100° C., and most preferably in the range of about 35° to about 85° C.

One of the major advantages of the instant process is the fast reaction rate achieved through the use of the alkali metal tetrafluoroborate catalyst. The time for the reaction to run to completion, of course, will vary depending on the temperature conditions employed, the concentration of the reactants and catalyst, and the particular catalyst and reactants employed. Generally, however, the reaction is fully completed in less than about 10 hours. Completion of the reaction with excellent yields has also been achieved, however, in reaction times of less than five hours, e.g., from two to five hours. Therefore, the reaction time employed is generally in the range from about 1 to about 10 hours, and most preferably in the range of about two to about five hours.

Once the reaction has run to completion, water can be added to the reaction product mixture in order to separate the catalyst, residual hydrogen chloride, and much of the ether solvent from the desired aryl sulfide product. The addition of the water generally results in the precipitation of the aryl sulfide product, which can then be readily isolated via filtration. The catalyst and ether solvent can be recovered from the water by conventional techniques.

The solid substituted aryl sulfide product can then be further purified by washing with a suitable wash solution, e.g., a sodium carbonate or sodium hydroxide solution. This washing should remove all remaining traces of by-product hydrogen chloride. Other conventional recovery and purification techniques might also be employed. Depending on the solubility of the specific aryl sulfide product, conventional concentration techniques might be suitably employed. For example, recrystallization from a low molecular weight alcohol such as ethanol.

The diaryl and oligomeric substituted aryl sulfide products obtained via the instant invention find particular applicability in the polymer resin field. For example, the oligomeric products find particular importance as epoxy resin curing agents and as cure accelerators in other polymer systems. They may also be used as hydrolyzed or partially hydrolyzed precursors for the liberation of free amino groups. The diaryl sulfides find utility as precursors for commercially valuable diaryl sulfoxides and sulfones. More specifically, 4,4'-bisacetamidodiphenyl, which can be easily prepared by the process of the instant invention, is a precursor for the well known 4,4'-diaminodiphenylsulfone, which is widely used in epoxy and other resin systems.

The following examples are given as specific illustrations of the instant invention. It should be understood, however, that the specific details set forth in the examples are merely illustrative and in nowise limitative. All parts and percentages in the examples and the remainder of the specification are by weight unless otherwise specified.

EXAMPLE 1

Example 1 illustrates the operability of the instant process by preparing 4,4'-diacetamidodiphenyl sulfide from acetanilide.

A multi-necked flask is immersed in a water bath which can control the flask temperature from −10° to 90° C. as desired. The flask is fitted with an inert gas (argon) tube, a glass thermowell containing a thermocouple for continuously monitoring the temperature, a stirrer shaft and blade, a condenser fitted with a drying agent protective tube, and an addition tube. To the flask is added acetanilide; 54 g (0.40 mole) of 260 ml of 1,2-dichloroethane; 100 ml of triethylene glycol dimethyl ether; and 44 g (0.40 mole) of sodium tetrafluoroborate. This mixture is sparged 15 minutes while 20.6 g (0.20 mole) of sulfur dichloride in 50 ml of 1,2-dichloroethane is charged to the addition tube. The sulfur dichloride solution is added slowly over one hour. The temperature is then increased to 85° C. and held for 3 hours. The solution is filtered to remove some precipitated 4,4′-diacetamidodiphenyl and the filtrate is reduced to 50% of its original volume in vacuo. The remaining solution is poured into water to produce more 4,4′-diacetamidodiphenyl to give overall 48.7 g (81% yield) of product, m.p. 195°–197° C. The structure and purity are confirmed by Fourier Transform Infrared Spectroscopy and proton Nuclear Magnetic Resonance.

COMPARATIVE EXAMPLE 1

This comparative example illustrates the effect of conducting the coupling reaction of acetanilide to form 4,4′-acetamidodiphenyl sulfide in the absence of a lithium or sodium tetrafluoroborate catalyst and an ether comprising solvent therefor. The procedure of Example 1 is followed.

Acetanilide (54 g) is dissolved in 350 ml of chloroform with 20.6 g of sulfur dichloride being added thereto, dropwise, over thirty minutes. The solution is held at 45° C. overnight. The precipitated product is filtered and recrystallized from ethanol/water in a 26% yield. The crude melting point thereof equals 187° C.

As can be seen from the aforegoing experimental run, the high yield and high rate of reaction demonstrated in Example 1 is not obtained in the absence of the tetrafluoroborate catalyst.

COMPARATIVE EXAMPLE 2

This comparative example illustrates the difficulties encountered when a standard Lewis acid catalyst is utilized in an attempted coupling of acetanilide.

Following the procedure of Example 1, 233.5 g of acetanilide in 1.2 liters of 1,2-dichloroethane with 6.7 g of ferric chloride are treated dropwise with 84.7 g (55 ml) of sulfur dichloride at room temperature. After the addition of 10 ml of sulfur dichloride there is no evidence of reaction and the temperature is raised to 45° C. In successive portions, 324 g of additional ferric chloride are added over the next two hours with no evidence of reaction. The addition of sulfur dichloride is then resumed and the temperature increased. After one hour the temperature is 82° C. (reflux). Reflux is continued an additional 20 hrs. After the standard work up, only a black semi-solid mass could be obtained. Repeated charcoal treatments and recrystallizations on a portion eventually yields only acetanilide.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A process for the synthesis of an aryl sulfide substituted with an alkanoylamino or (N-alkyl)alkanoylamino substituent which comprises reacting a sulfur dihalide with an aromatic reactant compound of the structural formula

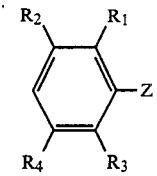

wherein $R_1$, $R_2$, $R_3$, and $R_4$, which can be the same or different, represent hydrogen or lower alkyl, and Z is

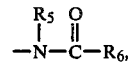

wherein $R_5$ represents hydrogen or a lower alkyl and $R_6$ a lower alkyl, in the presence of a catalytic amount of an alkali metal tetrafluoroborate catalyst wherein said alkali metal is selected from the group consisting of lithium and sodium, and an ether comprising solvent capable of solvating said reactants and catalyst sufficiently to allow said reacting to occur.

2. The process of claim 1 wherein the aryl sulfide is a diarylsulfide.

3. The process of claims 1 or 2 wherein the sulfur dihalide is sulfur dichloride.

4. The process of claim 2 wherein said aromatic compound which acts as a reactant is acetanilide and wherein the diaryl sulfide formed is 4,4′-diacetamidodiphenyl sulfide.

5. The process of claim 1 wherein said ether comprising solvent comprises an halogenated hydrocarbon-ether mixture.

6. The process of claim 5 wherein said solvent consists of a mixture of 1,2-dichloroethane and triethylene glycol ether in a volume ratio of about 1:1 to about 5:1.

7. The process of claim 6 wherein the said ratio is in the range of about 2:1 to about 4:1.

8. The process of claim 1 wherein said catalyst is sodium tetrafluoroborate.

9. The process of claim 2 wherein the mole ratio of the aromatic compound to sulfur dihalide is at least about 2:1 and the amount of catalyst employed is from 10 mole to about 300 mole percent based on the molar amount of sulfur dihalide.

10. The process of claim 9 wherein said molar ratio of aromatic compound to sulfur dichloride is about 2:1 and said molar amount of catalyst based on the amount of sulfur dichloride is from about 150 to about 250 mole percent.

11. The process of claim 1 wherein said reaction is conducted at a temperature in the range of about 0° to 110° C. for a length of time ranging from about 1 to about 10 hours.

12. The process of claim 11 wherein said temperature is in the range of from about 0° to 100° C. and said reaction time ranges from about two to about five hours.

13. The process of claim 11 wherein said temperature is in the range of from about 35° to 85° C.

14. The process of claim 3 wherein acetanilide is reacted with sulfur dichloride with the mole ratio of the acetanilide to sulfur dichloride being at least about 2:1, said reaction occurring in the presence of a catalytic amount of an alkali metal tetrafluoroborate catalyst and an ether comprising solvent comprising a halogenated hydrocarbon-ether mixture, and wherein said reaction is conducted at a temperature in the range of about 0° to 110° C. and for a length of time ranging from about 1 to about 10 hours.

15. The process of claim 14 wherein the molar ratio of the acetanilide to sulfur dichloride is about 2:1, said catalyst is sodium tetrafluoroborate and is employed in an amount in the range of about 10 to about 300 mole percent based on the amount of sulfur dichloride, the temperature is in the range of about 35° to 85° C. and the reaction is conducted for a period of time ranging from about 2 to about 5 hours.

16. The process of claim 14 or 15 wherein said ether comprising solvent consists essentially of a mixture of dichloroethane and triethylene glycol ether in a volume ratio of about 2:1 to about 4:1.

17. The process of claim 1 wherein the aryl sulfide is an oligomer.

18. The process of claim 17 wherein the mole ratio of the aromatic compound to sulfur dihalide is greater than 1:1 but less than about 2:1 and the amount of catalyst employed is from 10 to about 300 mole percent based on the molar amount of sulfur dihalide.

19. The process of claim 17 or 18 wherein the sulfur dihalide is sulfur dichloride.

* * * * *